United States Patent
Gorman

(10) Patent No.: US 10,959,876 B2
(45) Date of Patent: Mar. 30, 2021

(54) DENTAL APPLIANCE

(71) Applicant: Martin N. Gorman, Encino, CA (US)

(72) Inventor: Martin N. Gorman, Encino, CA (US)

( * ) Notice: Subject to any disclaimer, the term of this patent is extended or adjusted under 35 U.S.C. 154(b) by 676 days.

(21) Appl. No.: 15/706,421

(22) Filed: Sep. 15, 2017

(65) Prior Publication Data

US 2018/0000630 A1 Jan. 4, 2018

Related U.S. Application Data

(62) Division of application No. 14/122,245, filed as application No. PCT/US2012/040176 on May 31, 2012, now abandoned.

(60) Provisional application No. 61/492,117, filed on Jun. 1, 2011.

(51) Int. Cl.
*A61F 5/56* (2006.01)
*A61M 16/00* (2006.01)

(52) U.S. Cl.
CPC ......... *A61F 5/566* (2013.01); *A61M 16/0057* (2013.01)

(58) Field of Classification Search
CPC .. A61F 5/56–58; A61M 16/0057; A61C 7/08; A61C 19/063; A61C 19/066; A61C 5/90; A63B 71/085; A63B 2071/086; A63B 2071/088; A61K 9/006
USPC ...................................................... 433/140
See application file for complete search history.

(56) References Cited

U.S. PATENT DOCUMENTS

| | | | | |
|---|---|---|---|---|
| 4,615,697 A * | 10/1986 | Robinson | ............. | A61K 9/5026 424/423 |
| 5,108,286 A * | 4/1992 | Freedman | ............. | A61C 9/0006 433/37 |
| 5,915,385 A * | 6/1999 | Hakimi | ............. | A61F 5/566 128/848 |
| 6,136,297 A | 10/2000 | Sagel et al. | | |
| 6,276,937 B1 * | 8/2001 | Gasman | ............. | A61C 13/0025 433/168.1 |
| 6,467,485 B1 | 10/2002 | Schmidt | | |
| 7,730,890 B2 | 6/2010 | Enoch | | |
| 2002/0103219 A1 * | 8/2002 | Jacob | ............. | A61K 31/4741 514/291 |
| 2005/0186288 A1 | 8/2005 | Chiou et al. | | |

(Continued)

FOREIGN PATENT DOCUMENTS

| | | |
|---|---|---|
| JP | 2001-161736 A | 6/2001 |
| WO | WO-98/55079 A2 | 12/1998 |
| WO | WO-2009/158584 A1 | 12/2009 |

OTHER PUBLICATIONS

Examination Report dated Oct. 13, 2016 received in corresponding European Application No. 12793854.6, 4 pages.

(Continued)

*Primary Examiner* — Keri J Nelson
*Assistant Examiner* — Michelle J Lee
(74) *Attorney, Agent, or Firm* — Foley & Lardner LLP

(57) ABSTRACT

A dental appliance is provided. The dental appliance includes a dental form configured to receive a portion of a dental arch of an individual, and an adhesive strip comprising a first side and a second side. The first side of the adhesive strip is attached to a portion of the dental form. The second side of the adhesive strip comprises a mucoadhesive configured to adhere the adhesive strip to a tongue of the individual such that the tongue of the individual can be selectively attached to the dental appliance.

13 Claims, 4 Drawing Sheets

(56) References Cited

U.S. PATENT DOCUMENTS

| | | | |
|---|---|---|---|
| 2007/0048347 | A1 | 3/2007 | Bardach et al. |
| 2007/0289600 | A1 | 12/2007 | Li |
| 2008/0043132 | A1 | 2/2008 | Gunter |
| 2008/0082041 | A1 | 4/2008 | Hausmann et al. |
| 2009/0060958 | A1 | 3/2009 | Mello et al. |
| 2009/0120448 | A1 | 5/2009 | Keropian |
| 2009/0178684 | A1 | 7/2009 | Greenburg |
| 2009/0181071 | A1 | 7/2009 | St. John et al. |
| 2013/0078197 | A1 | 3/2013 | Mello et al. |

OTHER PUBLICATIONS

International Search Report and Written Opinion dated Aug. 31, 2012, as received in corresponding International Patent Application No. PCT/US2012/040176.

Office Action dated Dec. 4, 2016, in corresponding Israel Application No. 229461, 3 pages.

Office Action dated Jul. 5, 2016, received in corresponding Russian Application No. 2013157327 (089401) (8 pages) and English translation (6 pages).

Office Action dated Mar. 7, 2016, in corresponding Australian application No. 2012262223, 3 pages.

Office Action in Russian Application No. 2013157327 dated Mar. 18, 2016, and English translation, 14 pages.

Supplementary European Search Report dated Mar. 10, 2015, in corresponding European Application No. 12793854.6, 9 pages.

Supplementary Partial European Search Report dated Nov. 19, 2014.

U.S. Office Action on U.S. Appl. No. 14/122,245 dated Dec. 27, 2016.

U.S. Office Action on U.S. Appl. No. 14/122,245 dated Jun. 15, 2017.

U.S. Office Action on U.S. Appl. No. 14/122,245 dated Jun. 28, 2016.

U.S. Office Action on U.S. Appl. No. 14/122,245 dated Sep. 24, 2015.

Examination Report dated May 7, 2018 in corresponding Canadian application No. 2,836,794, 4 pages.

Examination Report dated Feb. 8, 2019, received in corresponding Canadian application No. 2,836,794, 3 pages.

* cited by examiner

DENTAL APPLIANCE

CROSS-REFERENCE TO RELATED APPLICATIONS

The present application claims a priority benefit, under 35 U.S.C. §120, as a divisional application of U.S. patent application Ser. No. 14/122,245 filed Jan. 15, 2014, entitled "DENTAL APPLIANCE" which is a U.S. National Stage of International Application No. PCT/US2012/040176 filed on May 31, 2012, which claims priority from U.S. Provisional Application No. 61/492,117, filed Jun. 1, 2011, all of which are hereby incorporated by reference in their entireties.

FIELD OF THE INVENTION

The present invention relates generally to the field of dental appliances and, more particularly, to dentally retained intraoral appliances worn at night for treatment of snoring and obstructive sleep apnea.

BACKGROUND OF THE INVENTION

Obstructive sleep apnea is a serious and potentially lethal disorder characterized by abnormal pauses in breathing or instances of abnormally low breathing. Each pause in breathing, called an apnea, can last from a few seconds to several minutes, and may occur 5 to 30 times or more per hour. Individuals with sleep apnea can experience daytime fatigue, impaired reaction time and vision problems. Other effects include difficulty with information processing, judgment, and short term memory, all of which can severely interrupt daytime cognition. Behavioral effects, such as decreased motivation, moodiness, and aggressiveness may also accompany sleep apnea. The behavioral and cognitive effects of sleep apnea can be dangerous in many occupations especially manual labor and machine operating.

Snoring is the vibration of respiratory structures and the resulting sound, due to obstructed air movement during breathing while sleeping. In some cases the sound may be soft, but in other cases, it can be loud and unpleasant. Snoring, like sleep apnea, can cause sleep deprivation to snorers and those around them, as well as daytime drowsiness, irritability, and lack of focus.

Some studies reveal that habitual snoring and sleep apnea are associated with other potentially serious medical conditions, such as hypertension, ischemic heart disease, and strokes. Accordingly, early diagnosis and treatment is recommended.

Snoring and obstructive sleep apnea are typically caused by partial or complete obstruction of an individual's pharyngeal airway. Airway obstruction often results from the apposition of the rear portion of the tongue with the posterior pharyngeal wall.

One approach for the treatment of sleep apnea and snoring is the performance of a surgery called uvulopalatopharyngoplasty, which is a procedure used to remove tissue in the throat. For example, a portion of the soft palate may be removed to prevent closure of the pharyngeal airway during sleep. However, the operation is not always successful and can result in complications.

Many non-surgical approaches for the treatment of sleep apnea and snoring have been developed, some of which involve the use of intraoral dental appliances. For example, it is recognized that movement of the lower jaw forward relative to the upper jaw can help to reduce sleep apnea and snoring by causing the pharyngeal airway to remain open.

Dental appliances have been developed which can be worn at night to maintain the upper and lower jaws in desired locations. Such appliances generally include orthodontic retainers or mouthguards that are custom-fit to an individual's upper (superior) and lower (inferior) dental arches.

While such dental appliances have proven effective in maintaining the lower jaw in a protruded position relative to the lower jaw, this position often results in serious discomfort in many individuals. The appliances are often bulky, invasive and constricting, and can cause pain in the jaw muscles. Use of such appliances can cause temporomandibular joint disorder (TMJ), an acute or chronic inflammation of the temporomandibular joint, which connects the mandible to the skull.

Therefore, there is a need for an improved dental appliance for treating sleep apnea and snoring.

SUMMARY OF THE INVENTION

According to one embodiment, a dental appliance includes a dental form configured to receive a portion of a dental arch of an individual, and an adhesive strip comprising a first side and a second side. The first side of the adhesive strip is attached to a portion of the dental form. The second side of the adhesive strip comprises a mucoadhesive configured to adhere the adhesive strip to a tongue of the individual such that the tongue of the individual can be selectively attached to the dental appliance.

According to another embodiment, a device includes an adhesive strip comprising a first side and a second side. The first side of the adhesive strip comprises an adhesive configured to attach the adhesive strip to a dental form configured to receive a portion of a dental arch of an individual. The second side of the adhesive strip comprises a mucoadhesive configured to attach the adhesive strip to a tongue of the individual such that the tongue of the individual can be selectively attached to the dental form.

According to another embodiment, a kit includes a dental form configured to receive a portion of a dental arch of an individual, and at least one adhesive strip comprising a first side and a second side. The first side of the adhesive strip comprises an adhesive configured to attach the adhesive strip to a dental form configured to receive a portion of a dental arch of an individual. The second side of the adhesive strip comprises a mucoadhesive configured to attach the adhesive strip to a tongue of the individual such that the tongue of the individual can be selectively attached to the dental form.

According to another embodiment, a device includes an adhesive strip comprising a first side and a second side. The first side of the adhesive strip comprises a first mucoadhesive configured to attach the adhesive strip to the teeth or an individual such that the adhesive strip can be selectively attached to the teeth. The second side of the adhesive strip comprises a second mucoadhesive configured to attach the adhesive strip to a tongue of the individual such that the tongue of the individual can be selectively attached to the dental form.

According to another embodiment, a method includes providing an adhesive strip comprising a first side and a second side, wherein the first side of the adhesive strip comprises an adhesive, and wherein the second side of the adhesive strip comprises a mucoadhesive configured to removable attach the adhesive strip to a tongue of the individual such that the tongue of the individual can be selectively attached to the dental form. The method further includes attaching the first side of the adhesive strip to an item via the adhesive, the item being selected from the group consisting of a dental form, teeth of an individual, a device extending across the mouth of an individual, a mandibular advancement device, or a continuous positive airway pressure (CPAP) device. The method further includes attaching the second side of the adhesive strip to a tongue of the individual via the mucoadhesive.

BRIEF DESCRIPTION OF THE DRAWINGS

The accompanying drawings, which are incorporated in and constitute a part of this specification, illustrate various embodiments of the present invention, and together with the description, serve to explain the principles of the invention. In the drawings.

DETAILED DESCRIPTION OF THE PREFERRED EMBODIMENTS

Embodiments of the disclosure will be described below with reference to the accompanying drawings. It should be understood that the following description is intended to describe exemplary embodiments, and not to limit the claimed subject matter.

Reference will now be made in detail to the present embodiments of the invention, examples of which are illustrated in the accompanying drawings. Wherever possible, the same reference numbers will be used throughout the drawings to refer to the same or like parts.

Figure 1:
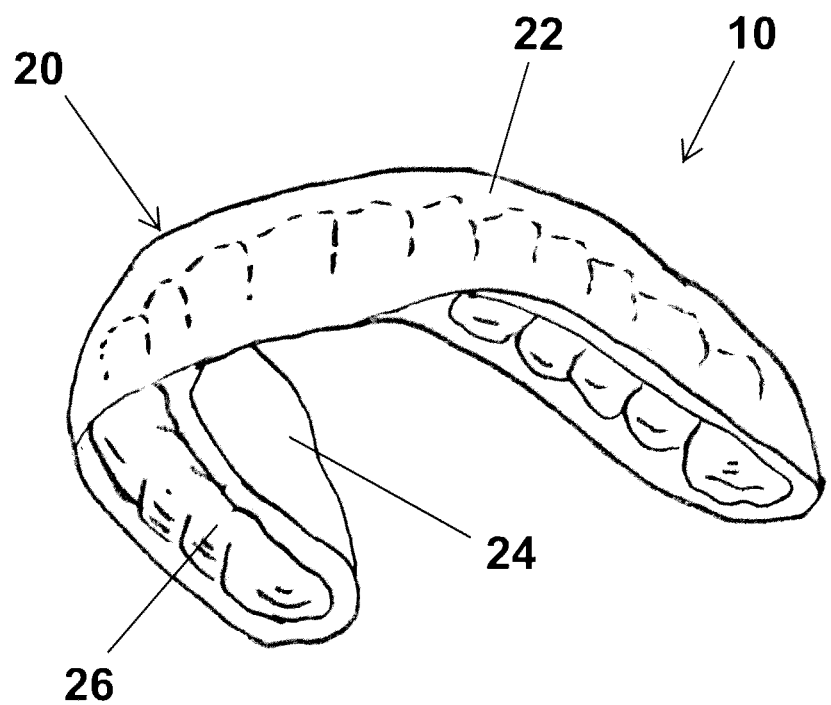
FIG. 1 is a bottom perspective view of a dental appliance according to an embodiment of the present invention.
Figure 2:
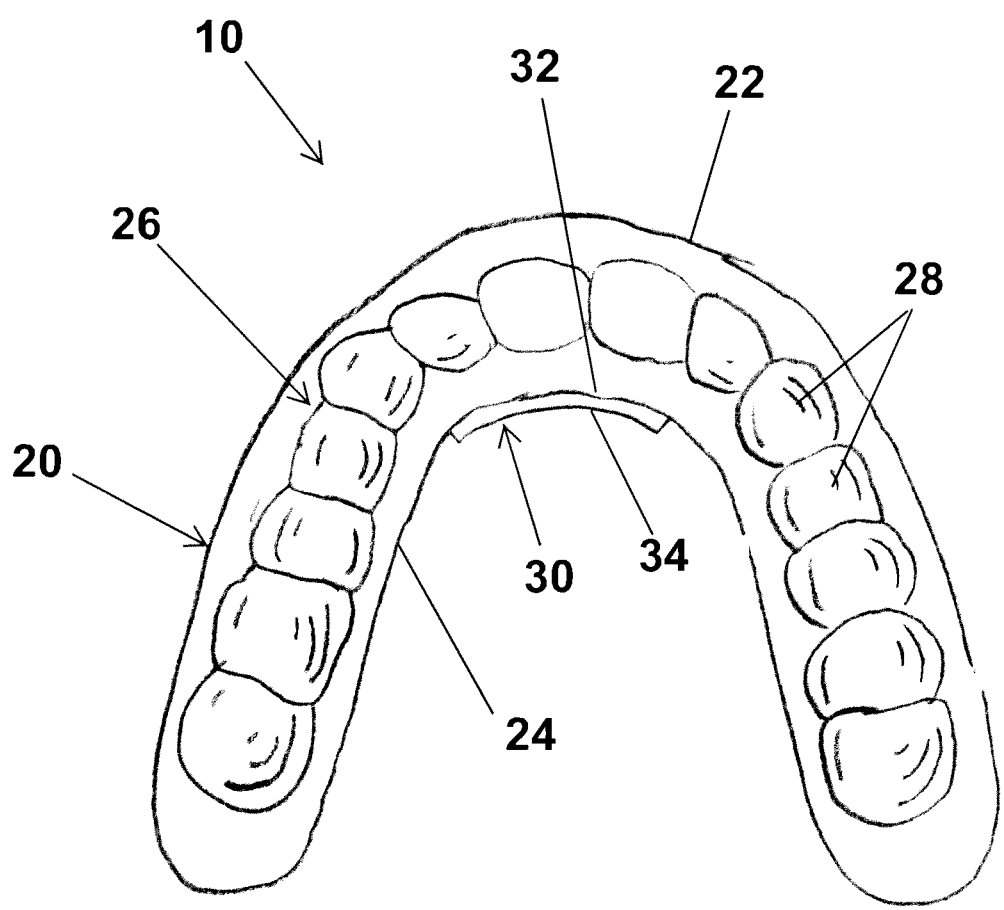
FIG. 2 is a top view of dental appliance according to an embodiment of the present invention, showing a dental form having an adhesive strip on a portion thereof.
Figure 3:
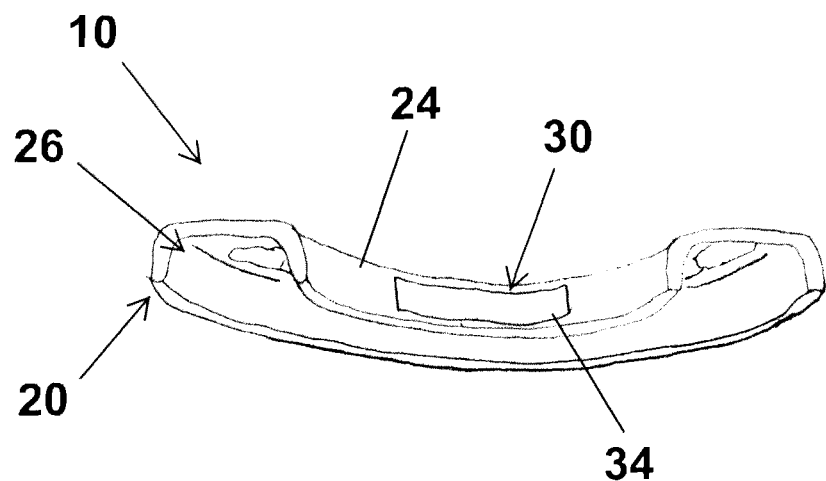
FIG. 3 is a rear perspective view of the dental appliance depicted in FIG. 2.

In an embodiment of the invention, depicted in FIGS. 1-3, a dental appliance 10 is provided. The dental appliance 10 includes a dental form 20 configured to receive a portion of a dental arch of an individual, and an adhesive strip 30 (see FIGS. 2 and 3) comprising a first side 32 and a second side 34. The first side 32 of the adhesive strip 30 is attached to a portion of the dental form 20. The second side 34 of the adhesive strip 30 comprises a mucoadhesive 35 (see FIG. 4) configured to adhere the adhesive strip 30 to a tongue of the individual such that the tongue of the individual can be selectively attached to the dental appliance 10.

The dental form 20 may have a front exterior wall 22 and a rear exterior wall 24. The dental form can be configured to receive a portion of the inferior dental arch and/or the superior dental arch of an individual. The rear exterior wall 24 is the wall that is on the tongue side of the dental form 20 if the dental form is configured to receive the inferior dental arch, and is on the palatal side of the dental form 20 if the dental form is configured to receive the superior dental arch. The front exterior wall 22 opposes the rear exterior wall. The dental form 20 is configured to receive the dental arch of an individual in a groove 26. The dental form 20 may be a custom dental form that is custom made for an individual using a mold of the superior or inferior dental arch of the individual. In this case, the dental form 20 may include a series of indentations 28 that match the shape of an individual's teeth, and thus provide them with a stable fitted surface. The dental form 20 may be thin, so as to provide comfort to an individual when using the dental appliance 10. For example, the dental form may have interior and exterior walls that have a thickness between 0.5 mm and 1.0 mm. The dental form 20 may be transparent so as to be more aesthetically pleasing during use. The dental form 20 may be made of a plastic material, such as an acrylic resin. An example of a suitable acrylic resin is Biocryl™, manufactured by Great Lakes Orthodontics.

The dental form 20 may be formed using methods known in the art. For example, an impression of the superior or inferior dental arch of an individual may be made to create a mold. A thin plastic piece (for example, between 0.5 mm and 1.0 mm in thickness) may be heated and molded to match the impression of the dental arch using a vacuum machine, creating a custom dental form 20. The adhesive strip 30 may be attached to the dental form 20 on an appropriate portion of the dental form 20.

Figure 4:
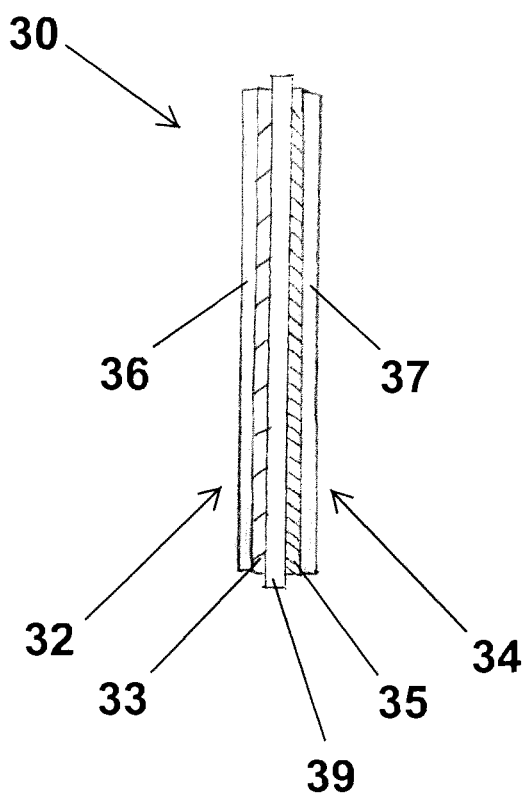
FIG. 4 is a side view of an adhesive strip of embodiments of the present invention.

The dental appliance 10 includes an adhesive strip 30 having a first side 32 and a second side 34, as shown in FIG. 4. The adhesive strip 30 is attached to the dental form 20 on a portion of the dental form 20. The adhesive strip 30 may be attached to the dental form 20 on the rear exterior wall 24 of the dental form 20. The first side 32 of the adhesive strip 30 is coated with an adhesive 33. The adhesive 33 may be any adhesive that is appropriate to removably attach the adhesive strip 30 to the dental form 20. The adhesive 33 may removably attach the adhesive strip 30 such that the adhesive strip 30 remains connected to the dental form 20 while in use, but a user can remove the adhesive strip 30 from the dental form 20 when desired after use. The adhesive 33 may be, for example, an acrylic pressure-sensitive adhesive (PSA), a natural rubber PSA, a synthetic rubber PSA, or a UV curable PSA. Examples of synthetic rubber pressure-sensitive adhesives include those based on block copolymer rubbers, such as styrene-butadiene-styrene and styrene-isoprene-styrene; and those based on random copolymer rubbers such as styrene-butadiene-rubber. The adhesive 33 may be, for example, a synthetic rubber hydrocarbon resin that is latex free. The second side 34 of the adhesive strip 30 is coated with a mucoadhesive 35 that can attach the second side 34 of the adhesive strip 30 to the tongue of an individual. The mucoadhesive 35 removably attaches the adhesive strip 30 to the tongue such that the tongue will remain connected to the adhesive strip 30 while in use, but a user can remove the tongue from the adhesive strip 30 when desired after use. Examples of such mucoadhesives include cellulose based adhesives, chitosan, carboxyl methyl cellulose, hydroxypropyl methyl cellulose, and synthetic polypectins. The mucoadhesive 35 may include a material for absorbing moisture, such as cellulosics, sugars, starches, proteins. The mucoadhesive 35 may include a synthetic elastomeric block copolymer rubber PSA (such as SBS or SIS, discussed above). The mucoadhesive may also include a tackifying resin. The mucoadhesive 35 may be configured to remain active for between 6 and 10 hours, and preferably between 8 and 10 hours. The adhesive strip 30 may be designed to be changed daily by a user. The mucoadhesive 35 may be flavored. As an example, the mucoadhesive used in the PerioPatch®, available from PeriZone®, may be used in embodiments of the invention. This mucoadhesive includes ethylcellulose (a cellulosic), polyacrylic acid (a super-hydrophilic synthetic polymer), sambucus nigra, castor oil (an alcohol-based natural oil used as a carrier), acacia gum, methyl hydroxylpropyl cellulose (a cellulosic), glycerol (an alcohol carrier), centella asiatica, titanium dioxide (a white pigment), echinacea purpurea, and polysorbate 80 (a sugar-based surfactant), as well as flavoring.

The adhesive 33 and mucoadhesive 35 may be provided on a suitable base strip 39. The base strip 39 can be formed of a single layer or can be formed by multiple layers connected together. The base strip 39 may, for example, be a single layer made of a synthetic moldable plastic material that is latex free. The base strip 39 may be made of, for example, a polyester film, a mylar film, a water-soluble film (such as polyvinyl alcohol), or a non-woven/natural fabric material. The mucoadhesive 35 may be provided with a protective layer 37 over the mucoadhesive 35 to protect the mucoadhesive 35 until the dental appliance 10 is to be used. The protective layer may be made of, for example, a paper or polyester material coated with a release coating (typically a silicon based release coating). The adhesive strip 30 may have any shape suitable for attaching to the dental form 20. For example, the adhesive strip 30 may have a square or rectangular shape. The size of the adhesive strip 30 may depend on the dimensions of the dental arches and/or tongue of the individual using the dental appliance 10.

In an embodiment of the invention, the adhesive strip 30 may be attached to a projection that extends from a portion of the dental form 20. For example, the adhesive strip 30 may be attached to a projection configured so as to extend towards the back of an individual's throat when the dental form 20 is placed in the mouth of an individual.

In an embodiment of the invention, the adhesive strip 30 may be attached to a portion of a traditional mandibular advancement device or a portion of a continuous positive airway pressure (CPAP) device, rather than a dental form.

In another embodiment of the invention, the adhesive strip 30 may be attached to a device configured to extend across the mouth of an individual. For example, the adhesive strip 30 may be attached to a rubber band or another soft or hard device configured to extend across the mouth. The device may, for example, extend between two sides of a dental form. The adhesive strip 30 may be attached, for example, to a transpalatal bar or restrainer of the devices discussed in U.S. Pat. No. 8,132,567 to Keropian, which is hereby incorporated by reference in its entirety. Use of the adhesive strip 30 can allow, for example, for use of a shortened restrainer, which can reduce the likelihood of gagging by reducing the extension of the restrainer into the throat.

In an embodiment of the invention, the adhesive strip 30 may be provided without being attached to a dental form 20, but can be configured to be used with an individual's existing intraoral dental appliance or dental form. The adhesive strip 30 may be provided with an adhesive 33 on the first side 32 of the adhesive strip 30 and a mucoadhesive 35 on the second side 34 of the adhesive strip 30. The adhesive 33 and mucoadhesive 35 may be provided on a suitable base strip 39. The adhesive 33 and mucoadhesive 35 may be provided with a protective layer 36 over the adhesive 33 and a protective layer 37 over the mucoadhesive 35, which can be removed by an individual before use of the adhesive strip 30. The individual can remove the protective layer 36 and attach the first side 32 of the adhesive strip 30 to an existing intraoral dental appliance or dental form (e.g., an existing retainer or mouthpiece). The individual may then remove the protective layer 37, place the existing dental appliance or dental form in the correct position in the mouth, and attach the tongue to the second side 34 of the adhesive strip 30.

In another embodiment of the invention, the adhesive strip 30 can be configured to be used without any dental appliance or dental form, i.e., the adhesive strip 30 can be configured to be connected to the tongue and directly to the teeth or other suitable portion of the person's mouth. In this configuration, preferably the adhesive 33 is replaced with an additional mucoadhesive that is removably attachable directly to the teeth of an individual. The additional mucoadhesive can comprise the same materials as the mucoadhesive 35, which include cellulose based adhesives, chitosan, carboxyl methyl cellulose, hydroxypropyl methyl cellulose, and synthetic polypectins. In this embodiment, the adhesive strip 30 has substantially the same configuration as that described in the preceding paragraph. The individual can remove the protective layer 37 from the mucoadhesive 35 and remove the protective layer 36 from the additional mucoadhesive. The individual can attach the first side 32 of the adhesive strip 30 directly to the teeth of the superior or inferior dental arch. The individual can then attach the tongue to the second side 34 of the adhesive strip 30. The adhesive strip 30 may comprise a first component strip forming the first side of the adhesive strip 30, and a second component strip forming the second side of the adhesive strip 30. The first component strip may comprise a first mucoadhesive, and the second component strip may comprise a second mucoadhesive, which is the same or different than the first mucoadhesive. The first component strip and the second component strip may be attached to one another via an adhesive. In other words, a double-sided mucoadhesive strip may be formed by attaching two single-sided mucoadhesive strips. For example, in this embodiment, the adhesive strip 30 may be made by joining two PerioPatch® devices to one another at their non-mucoadhesive sides.

In another embodiment of the invention, a kit is provided that includes both the dental form 20 and at least one adhesive strip 30 as described in the preceding paragraph.

Figure 5:
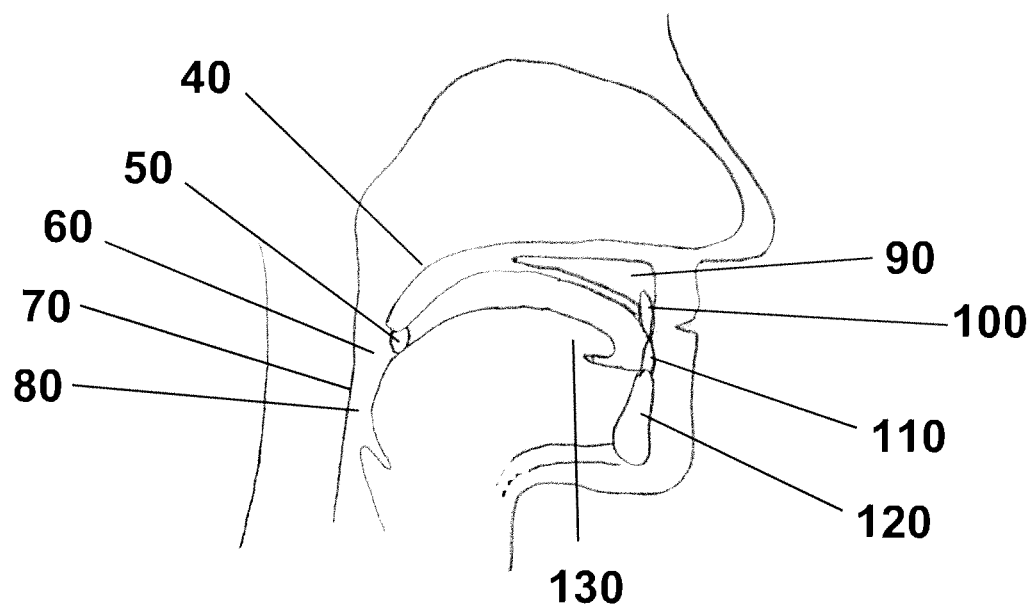
FIG. 5 is a side cross-sectional view of a head of an individual with a partially obstructed pharyngeal airway.
Figure 6:
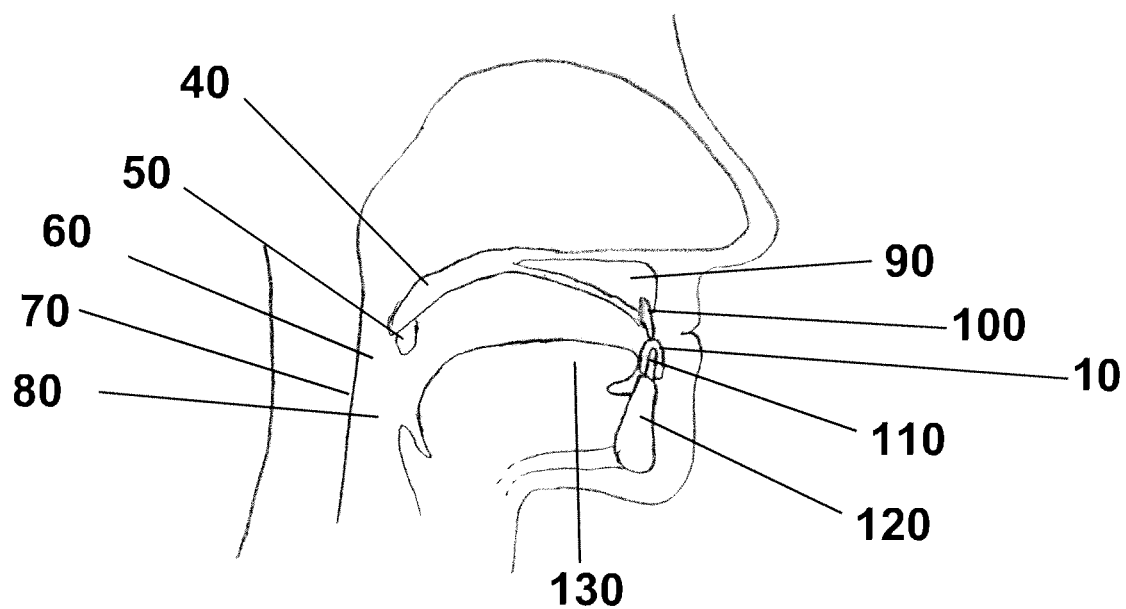
FIG. 6 is a side cross-sectional view of a head of an individual using an embodiment of the dental appliance of the present invention.

Rresults that can be obtained by the dental appliance 10 are depicted in FIGS. 5 and 6. While the results are shown in conjunction with the dental appliance, it is expected that the same results can be achieved by using the adhesive strip 30 with an individual's existing intraoral dental appliance or dental form or by using the adhesive strip 30 alone. FIG. 5 depicts a cross section of the head of an individual with a partially obstructed pharyngeal airway 60. FIG. 5 shows the soft palate 40, uvula 50, posterior pharyngeal wall 70, upper jaw 90, superior dental arch 100, inferior dental arch 110, lower jaw 120, and tongue 130 of an individual. FIG. 5 shows the tongue 130 partially obstructing the pharyngeal airway 60 between the tongue 130 and the pharyngeal wall 70. The pharyngeal airway 60 is narrow in the region 80, and the uvula 50 touches the tongue 130, both of which can cause sleep apnea and snoring.

FIG. 6 depicts a cross section of the head of an individual using the dental appliance 10. In FIG. 6, the dental appliance 10 is located on the inferior dental arch 110 of the individual. The tongue 130 adheres to the mucoadhesive 35 on the second side 34 of the adhesive strip 30. The dental appliance 10 can prevent the tongue 130 from collapsing backwards and blocking the pharyngeal airway 60 in the region 80, and can also prevent the uvula 50 from contacting the tongue 130, thus helping to treat sleep apnea and snoring. Because the dental appliance 10 is relatively thin, it allows a user to open and close the mouth and allows total freedom of movement of the jaw. While FIG. 6 shows the dental appliance 10 being used on the inferior dental arch 110, the dental appliance 10 can alternatively be provided on the superior dental arch 100, or the dental appliance 10 can be configured such that it is disposed on both the superior dental arch 100 and the inferior dental arch 110. For example, the dental appliance 10 may be provided on the superior dental arch 100 of an individual who normally breaths through the nose when sleeping. The dental appliance 10 may be provided on the inferior dental arch 110 of an individual who normally breaths through the mouth when sleeping.

While the preferred embodiments of the devices and methods have been described in reference to the environment in which they were developed, they are merely illustrative of the principles of the inventions. Modification or combinations of the above-described assemblies, other embodiments, configurations, and methods for carrying out the invention, and variations of aspects of the invention that are obvious to those of skill in the art are intended to be within the scope of the claims.

What is claimed is:

1. A method of treating snoring or sleep apnea, the method comprising: providing an adhesive strip comprising: a base strip having a first surface and a second surface opposing the first surface, a first mucoadhesive disposed on the first surface of the base strip, and a second mucoadhesive disposed on the second surface of the base strip; attaching the adhesive strip directly to teeth of an individual using the first mucoadhesive, and attaching the adhesive strip directly to the tongue of the individual using the second mucoadhesive, such that the tongue of the individual is attached to the teeth of the individual via the adhesive strip.

2. The method of claim 1, wherein the base strip is made of a synthetic moldable plastic.

3. The method of claim 2, wherein the synthetic moldable plastic is a polyester film, a mylar film, or a polyvinyl alcohol film.

4. The method of claim 1, wherein the tongue of the individual is attached to the teeth of the individual via the adhesive strip such that the tongue of the individual is prevented from collapsing backwards and blocking a pharyngeal airway of the individual.

5. The method of claim 1, wherein the tongue of the individual is attached to the teeth of the individual via the adhesive strip such that a uvula of the individual is prevented from contacting the tongue of the individual.

6. The method of claim 1, wherein the first and second mucoadhesives are configured to remain active for a time between 8 and 10 hours.

7. The method of claim 1, wherein the first and second mucoadhesives are made of a material selected from the group consisting of a cellulose based adhesive, chitosan, carboxyl methyl cellulose, hydroxypropyl methyl cellulose, a synthetic polypectin, and combinations thereof.

8. The method of claim 1, wherein the first mucoadhesive is the same as the second mucoadhesive.

9. The method of claim 1, wherein the base strip extends in a linear manner from a first longitudinal end thereof to a second longitudinal end thereof.

10. The method of claim 1, wherein the adhesive strip is rectangular.

11. The method of claim 1, wherein, in the step of attaching the adhesive strip to the teeth of the individual, the adhesive strip is attached to the superior dental arch.

12. The method of claim 1, wherein, in the step of attaching the adhesive strip to the teeth of the individual, the adhesive strip is attached to the inferior dental arch.

13. The method of claim 1, wherein the adhesive strip further comprises:
- a first protective layer disposed over the first mucoadhesive, and
- a second protective layer disposed over the second mucoadhesive,
- wherein the first and second protective layers are configured to be removed before use of the adhesive strip.

* * * * *